United States Patent
Lee et al.

(10) Patent No.: US 11,547,338 B2
(45) Date of Patent: Jan. 10, 2023

(54) ELECTRONIC FUNCTIONAL MEMBER, ELECTRONIC COMPONENT, AND WEARABLE DEVICE

(71) Applicant: JAPAN SCIENCE AND TECHNOLOGY AGENCY, Saitama (JP)

(72) Inventors: Sung Won Lee, Daegu (KR); Takao Someya, Tokyo (JP); Tsuyoshi Sekitani, Osaka (JP); Shinri Sakai, Yonezawa (JP)

(73) Assignee: JAPAN SCIENCE AND TECHNOLOGY AGENCY, Saitama (JP)

( * ) Notice: Subject to any disclaimer, the term of this patent is extended or adjusted under 35 U.S.C. 154(b) by 1086 days.

(21) Appl. No.: 16/304,094

(22) PCT Filed: May 27, 2016

(86) PCT No.: PCT/JP2016/065714
§ 371 (c)(1),
(2) Date: Nov. 21, 2018

(87) PCT Pub. No.: WO2017/203685
PCT Pub. Date: Nov. 30, 2017

(65) Prior Publication Data
US 2020/0323453 A1  Oct. 15, 2020

(51) Int. Cl.
*H05K 1/11* (2006.01)
*A61B 5/25* (2021.01)
*A61N 1/04* (2006.01)

(52) U.S. Cl.
CPC ............. *A61B 5/25* (2021.01); *A61N 1/048* (2013.01); *H05K 1/118* (2013.01);
(Continued)

(58) Field of Classification Search
CPC ....... H05K 1/036; H05K 1/0366; H05K 1/118
See application file for complete search history.

(56) References Cited

U.S. PATENT DOCUMENTS

2005/0235482 A1* 10/2005 Deaett ................. H01P 11/00
343/700 MS
2006/0040427 A1  2/2006 Ferrari
2016/0234932 A1*  8/2016 Oshima .............. H05K 3/4682

FOREIGN PATENT DOCUMENTS

JP  60-242693 A  12/1985
JP  64-049539 A   2/1989
(Continued)

OTHER PUBLICATIONS

Supplementary Partial European Search Report dated Jan. 2, 2020, issued in the corresponding European Application No. 169013166.3, filed Dec. 6, 2018, 8 pages.
(Continued)

Primary Examiner — Jeremy C Norris
(74) Attorney, Agent, or Firm — Christensen O'Connor Johnson Kindness PLLC (57) ABSTRACT

An electronic functional member according to the present embodiment includes a substrate; a fiber mesh comprising a fibrous resin composition that extends onto and is connected to the substrate; and a patterned conductive coating portion that coats one surface of a portion of the fiber mesh and that also extends onto the substrate.

8 Claims, 7 Drawing Sheets

(52) U.S. Cl.
CPC . *A61B 2562/0209* (2013.01); *A61B 2562/164* (2013.01); *H05K 2201/0278* (2013.01); *H05K 2201/10151* (2013.01)

(56) References Cited

FOREIGN PATENT DOCUMENTS

| JP | 06-319712 A | 11/1994 |
|---|---|---|
| JP | 07-222805 A | 8/1995 |
| JP | H08503875 A | 4/1996 |
| JP | 2002285342 A | 10/2002 |
| JP | 2003-127137 A | 5/2003 |
| JP | 2007-262623 A | 10/2007 |
| JP | 2010-501260 A | 1/2010 |
| JP | 2011-036524 A | 2/2011 |
| JP | 2011-125677 A | 6/2011 |
| JP | 3178230 U | 9/2012 |
| JP | 2013-021000 A | 1/2013 |
| JP | 2014-236103 A | 12/2014 |
| JP | 6444158 B | 12/2018 |
| WO | 94/22528 A1 | 10/1994 |
| WO | 2008/085199 A2 | 7/2008 |

OTHER PUBLICATIONS

Lee, Sungwon, et al., "A transparent bending-insensitive pressure sensor" Nature Nanotechnology, vol. 11, No. 5, Jan. 25, 2016, pp. 472-478, XP055541097, London ISSN: 1748-3387, DOI: 10.1038/nnano.2015.324.

Kim, Dae-Hyeong, et al., "Dissolvable films of silk fibroin for ultrathin conformal bio-integrated electronics", Nature Materials, vol. 9, No. 6, Apr. 18, 2010, pp. 511-517, XP055108265, ISSN: 1476-1122, DOI: 10.1038/nmat2745.

Hsu, P.-C., et al., "Performance Enhancement of Metal Nanowire Transparent Conducting Electrodes by Mesoscale Metal Wires," Nature Communications 4:2522, 2013.

International Search Report dated Aug. 9, 2016, issued in corresponding International Application No. PCT/JP2016/065714, filed May 27, 2016, 4 pages.

Notice of Allowance dated Oct. 30, 2018, issued in Japanese Application No. 2014-254072, filed Dec. 16, 2014, 6 pages.

Wu, H., et al., "A Transparent Electrode Based on a Metal Nanotrough Network," Nature Nanotechnology 8(6):421-425, Jun. 2013.

Extended European Search Report dated May 8, 2020, issued in corresponding EP Application No. 16903166.3, filed May 27, 2016, 10 pages.

Supplementary Partial European Search Report dated Jan. 2, 2020, issued in the corresponding European Application No. 16903166.3, filed Dec. 6, 2018, 8 pages.

Decision of Rejection dated Oct. 6, 2020, issued in corresponding Japanese Application No. 2018-518910, filed Jul. 12, 2018, 10 pages.

Notice of Reasons for Rejection dated Nov. 16, 2021, issued in related Japanese Patent Application No. 2020-192698, filed Nov. 19, 2020, 8 pages.

\* cited by examiner

ELECTRONIC FUNCTIONAL MEMBER, ELECTRONIC COMPONENT, AND WEARABLE DEVICE

TECHNICAL FIELD

The present invention relates to an electronic functional member, an electronic component and a wearable device.

BACKGROUND ART

In recent years, flexible electronics, which have various applications due to the softness of the materials, have been the focus of much attention. In particular, with the ageing of society worldwide, the level of interest is rising in the healthcare field. For example, flexible electronics have attracted attention as means for directly obtaining biometric information from cells and tissues by being worn on the surface of or inside the human body.

In general, flexible electronics are prepared by forming electronic devices on flexible substrates, but the pliability thereof cannot be considered to be sufficient. For this reason, the surface conformability cannot be considered to be adequate, and it is not possible to obtain information with high precision or to adequately reduce the sense of discomfort when worn or the like.

In order to solve this problem, biometric electrodes in which a holding unit having elasticity is enclosed in a detection unit have been disclosed (e.g., Patent Document 1). In these biometric electrodes, the detection unit encloses the holding unit having elasticity when the detection unit is brought into contact with a living body. For this reason, the holding unit deforms in response to pressure, thereby increasing the surface conformability of the detection unit.

Additionally, an arm cover for a myoelectric prosthetic arm into which wiring is woven (e.g., Patent Document 2) and a contact-wire working electrode (e.g., Patent Document 3) having metal-plated conductive fibers woven at regular intervals into a cloth-type fabric have been disclosed. In Patent Document 2, by weaving the wires with each other, the rigidity of each wire is reduced, thereby raising the surface conformability. Additionally, in Patent Document 3, the surface conformability is raised by weaving the metallic fibers into the cloth-type fabric.

Aside therefrom, biometric thin electrodes formed by bonding a pliable insulating synthetic resin film onto a hydroentangled non-woven fabric have been disclosed (e.g., Patent Document 4). This method raises the surface conformability by making use of the high deformability of hydroentangled non-woven fabrics.

Furthermore, Non-Patent Documents 1 and 2 disclose electrodes that have high surface conformability, formed by coating substrates with metallic nanowires.

RELATED LITERATURE

Patent Literature

[Patent Document 1]
JP 2011-36524 A
[Patent Document 2]
JP 2011-125677 A
[Patent Document 3]
JP 2007-262623 A
[Patent Document 4]
JP 7-222805 A

Non-Patent Literature

[Non-Patent Document 1]
Hui Wu et al., Nature Nanotechnology, vol. 8, pp. 421-425 (2013).
[Non-Patent Document 2]
Po-Chun Hsu et al., Nature Communications, 4:2522 (2013).

SUMMARY OF INVENTION

Technical Problem

However, the above-mentioned methods cannot be used to obtain electronic functional members having sufficiently high surface conformability, lateral stretchability, gas and moisture permeability, transparency and the like.

For example, in the biometric electrode disclosed in Patent Document 1, the detection unit makes contact with the living body with the holding unit sandwiched therebetween. For this reason, sufficient surface conformability cannot be obtained without pressure from the holding unit, so a load is applied to the living body. Additionally, the holding unit must have enough thickness and elasticity to obtain sufficient pressure, and thus becomes thick. Additionally, movement can cause the detection unit to slip, so stable measurements cannot be continuously obtained. Furthermore, the contact surface with the living body is covered by the detection unit and the holding unit, so the gas and moisture permeability cannot be considered to be sufficient. For this reason, the presence of moisture from perspiration or the like can cause the measurements to deviate or cause the electrode to separate from the contact surface. Such problems can be expected to become more prominent during long-term attachment.

In the methods disclosed in Patent Documents 2 and 3, wiring or metallic fibers having conductivity are woven in. However, since wiring and metallic fibers are themselves made from metal, they cannot be considered to have sufficient conformability or stretchability even in the form of thin wires. Additionally, when metallic fibers are woven in, it is difficult to freely design conductive patterns, making it difficult to obtain electronic functional members having complicated patterns.

Additionally, the biometric thin electrodes disclosed in Patent Document 4 are formed by laminating, onto a hydroentangled non-woven fabric, an insulating synthetic resin film that has pliability. The insulating synthetic resin is a film and is affixed to the surface to be measured, so sufficient gas and moisture permeability and transparency cannot be obtained.

In Non-Patent Documents 1 and 2, electrodes are produced by forming a fibrous substance on a film and further bonding a metal coating film thereon. However, if the metal coating film is brought into contact with the living body, the film is present on the back surface thereof. For this reason, the film covers the surface to be measured, and there cannot be considered to be sufficient gas and water permeability. In other words, the presence of moisture from perspiration or the like can cause the measurements to deviate or cause the electrode to separate from the contact surface.

Additionally, it is disclosed that the fibrous substance can be used as the electrode, but there are no descriptions of connections to external circuitry. Electrodes are only able to serve their functions by being connected to external circuitry by means of wiring or the like. For this reason, these electrodes must be connected to wiring or the like in the actual mode of use, and they must have connection portions at the connection areas. However, if there are connection portions, there is a risk of deterioration of electric properties due to contact resistance or the connection portions being separated by stresses associated with deformation.

The present invention was made in view of the above-described circumstances, and has the purpose of providing an electronic functional member, an electronic component and a wearable device having sufficiently high surface conformability, lateral stretchability, gas and moisture permeability, transparency and the like.

Solution to Problem

As a result of diligent investigation, the present inventors discovered the exceptional effect that an electronic functional member, an electronic component and a wearable device having sufficiently high surface conformability, lateral stretchability, gas and moisture permeability, and transparency can be provided by providing a film substrate; a fiber mesh formed from a resin composition; and a patterned conductive coating portion that coats at least one surface of a portion of the fiber mesh and that also extends onto the substrate.

Additionally, the present inventors discovered that an electronic functional member, an electronic component and a wearable device in which the fiber mesh is firmly held on the substrate can be provided by providing a substrate having an aperture portion; a fiber mesh formed from a resin composition that is suspended over the aperture portion with the substrate around the aperture portion as an outer frame; and a patterned conductive coating portion that coats one surface of a portion of the fiber mesh located over the aperture portion, and that also extends onto the substrate.

In other words, the following means were employed to solve the above-described problem.

(1) The electronic functional member according to one embodiment of the present invention comprises a substrate; a fiber mesh comprising a fibrous resin composition that extends onto and is connected to the substrate; and a patterned conductive coating portion that coats one surface of a portion of the fiber mesh and that also extends onto the substrate.

(2) The electronic functional member according to another embodiment of the present invention comprises a substrate having an aperture portion; a fiber mesh comprising a fibrous resin composition that is suspended over the aperture portion with the substrate around the aperture portion as an outer frame; and a patterned conductive coating portion that coats one surface of a portion of the fiber mesh located over the aperture portion, and that also extends onto the substrate.

(3) In the electronic functional members according to the above-described embodiments, the resin composition may be partially interlinked.

(4) In the electronic functional members according to the above-described embodiments, the resin composition may comprise a substance that is biodissolvable.

(5) In the electronic functional members according to the above-described embodiments, the aperture portion may have an aperture ratio of 10% to 99%.

(6) In the electronic functional members according to the above-described embodiments, a conductive coating forming the conductive coating portion may have a film thickness of 20 nm to 2000 nm.

(7) An electronic component according to an embodiment of the present invention has an electronic element connected to the conductive coating portion of the electronic functional member according to the above-described embodiments.

(8) A wearable device according to an embodiment of the present invention comprises the electronic functional member according to the above-described embodiments.

Advantageous Effects of Invention

The electronic functional member according to an embodiment of the present invention comprises a substrate; a fiber mesh comprising a fibrous resin composition; and a conductive coating portion that is formed as a single body extending across the substrate and the fiber mesh. Since the fiber mesh has high gas and moisture permeability, problems such as deviations in measurements or separation from the contact surface due to moisture from perspiration or the like will not occur. For this reason, highly precise measurements can be made over a long period of time. Additionally, the fiber mesh has exceptional pliability and can therefore function as an electronic functional member having high surface conformability with a lighter load. Furthermore, the conductive coating portion is patterned so as to coat one surface on the portion of the fiber mesh located over the aperture portion, and to also extend onto the substrate. Therefore, there are no connection portions at the interface between the fiber mesh and the substrate, and there is no need to consider problems such as the generation of contact resistance at the connection portions or the connection portions being broken or separated.

The electronic component according to an embodiment of the present invention has an electronic circuit element connected to the conductive coating portion of the above-mentioned electronic functional member. Examples of electronic circuit elements include chip elements such as ICs, LSIs, LEDs and photodiodes, and thin-film transistors on which insulating layers, organic semiconductor layers and the like are formed. By having the above-mentioned electronic functional member, it is possible to provide an electronic component that is soft and resistant to deformation or the like, and that is permeable to gas, moisture and light.

The wearable device according to an embodiment of the present invention comprises the above-mentioned electronic functional member. For this reason, it is possible to provide a wearable device having excellent surface conformability and stretchability, with less of a sense of attachment. Additionally, the gas and moisture permeability are high, so it is possible to prevent problems such as deviations in measurements or separation from the contact surface due to moisture from perspiration or the like, and to take stable measurements over a long period of time. Additionally, the device is transparent, so it is possible to observe or radiate light onto the contact surface through the electronic functional member.

DESCRIPTION OF EMBODIMENTS

Herebelow, the structures of the electronic functional member, the electronic component and the wearable device according to the present embodiment will be explained by referring to the drawings. The drawings used in the following description are sometimes shown with characterizing portions enlarged for convenience, in order to make the characteristics easier to understand, and the dimensional ratios of the constituent elements are not necessarily true to scale. The materials, dimensions and the like that are indicated in the following descriptions are merely exemplary, the present embodiment is not limited thereto, and the embodiments can be implemented with appropriate changes within a range not departing from the spirit of the invention. The electronic functional member, the electronic component and the wearable device of the present embodiment may comprise constituent elements such as components that are not described below, within a range not compromising the effects thereof (Electronic Functional Member)

Figure 1:
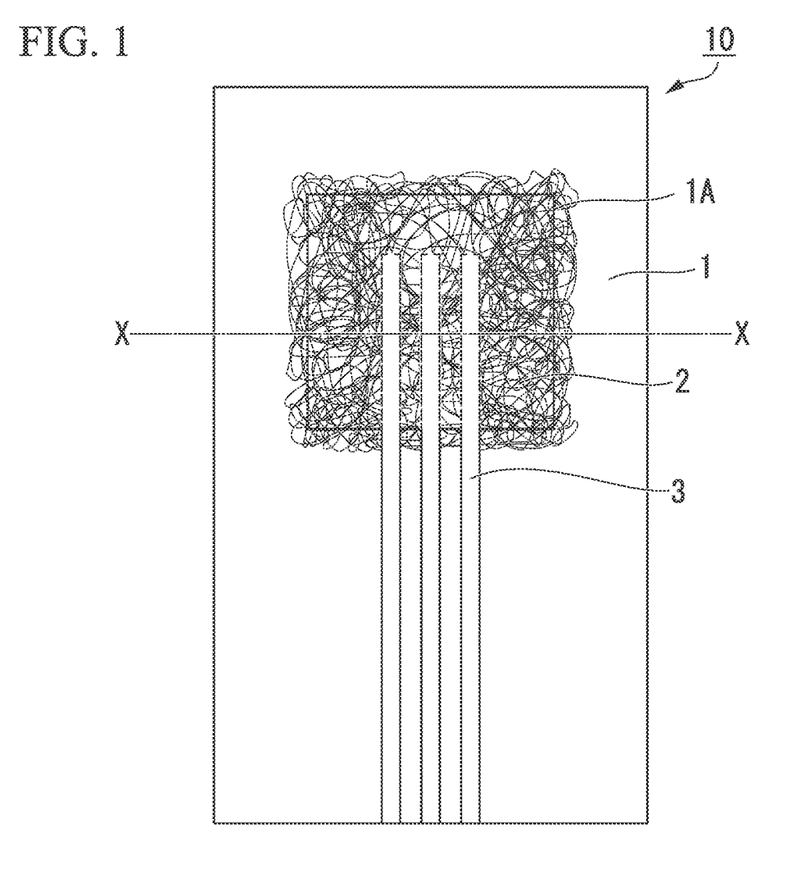
FIG. 1 is a schematic view of an electronic functional member according to an embodiment of the present invention.
Figure 2:
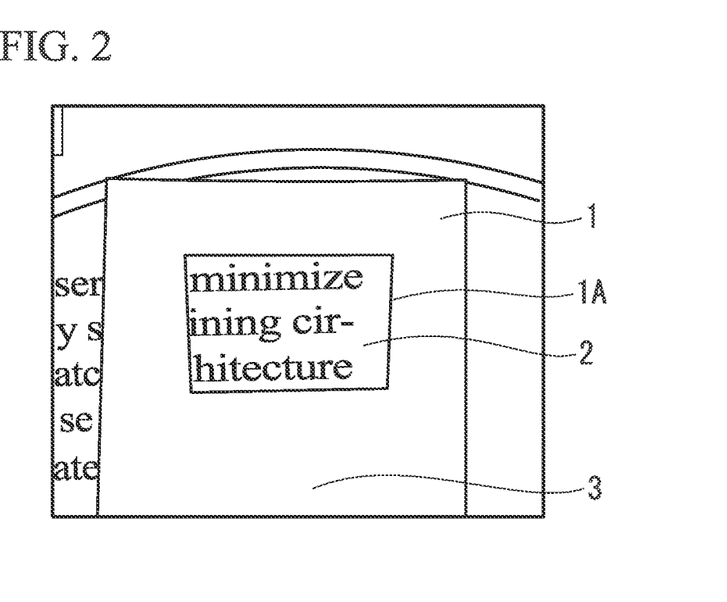
FIG. 2 is a photograph of an electronic functional member according to an embodiment of the present invention.

FIG. 1 is a schematic view of an electronic functional member according to one embodiment. FIG. 2 is a photograph of an electronic functional member according to one embodiment.

The electronic functional member 10 according to the one embodiment comprises a substrate 1 having an aperture portion 1A; a fiber mesh comprising a fibrous resin composition 2 that is suspended over the aperture portion with the substrate 1 around the aperture portion 1A as an outer frame; and a patterned conductive coating portion 3 that coats one surface of a portion of the fiber mesh located over the aperture portion 1A, and that also extends onto the substrate. In order to achieve a state of being "suspended over the aperture portion", the fibrous resin composition 2 is formed so as to be fixed to one of the surfaces of the substrate 1 and straddle the aperture portion.

The electronic functional member may, for example, be used as a component for receiving biometric information by coming into contact with a living body, a component for imparting an electrical signal to a living body, an electrode or the like.

In FIG. 1, the resin composition 2 is schematically illustrated as lines suspended over an aperture portion 1A in order to aid in understanding. The resin composition 2 may be in the form of straight lines or curved lines. Additionally, it may be suspended in a state of being stretched, by means of tension, from the outer frame and over the aperture portion, or may be suspended in a sagging state. For example, a fiber mesh formed from the resin composition 2 may be formed in the manner of cotton.

The conductive coating portion 3 is formed continuously across the surface of the substrate 1 and the resin composition fixed to the surface of the substrate 1. In FIG. 1, the conductive coating portion 3 is illustrated as three patterned lines, but it is not restricted to such a structure. For example, it may be patterned in a more complicated form, or may be formed from a single line. The conductive coating portion 3 need only be partially patterned. Additionally, the conductive coating portion 3 on the fiber mesh is illustrated by being enclosed in dotted lines. The reason dotted lines are used for illustration is that the fiber mesh has voids and the conductive coating portion 3 is therefore not formed in well-defined lines.

Figure 3:
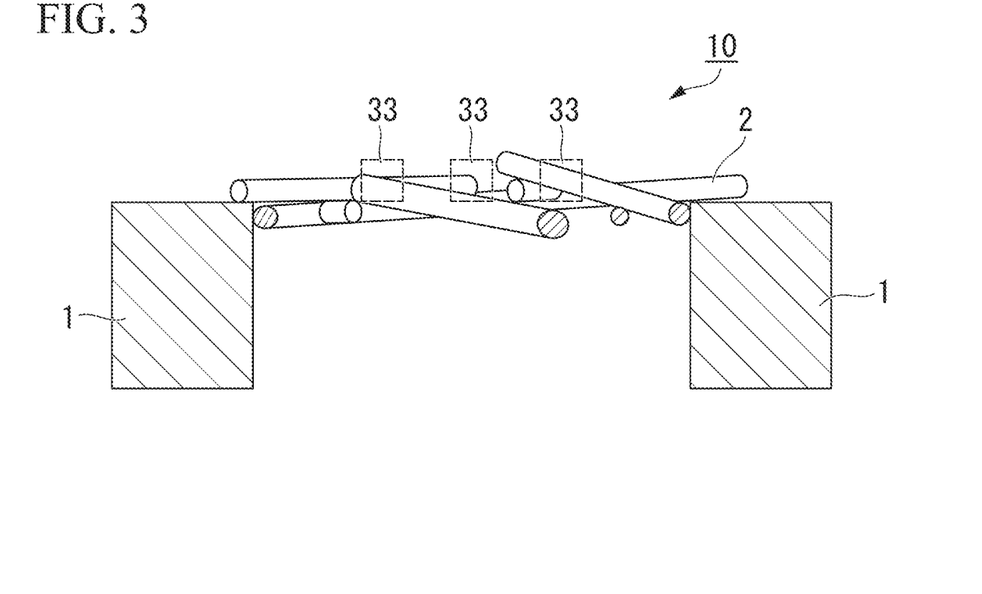
FIG. 3 is a schematic section view of a cross-section at X-X in the electronic functional member shown in FIG. 1.

FIG. 3 is a schematic section view showing a cross-section of the electronic functional member at the line X-X shown in FIG. 1. As shown in FIG. 3, the resin composition 2 is formed as a fiber mesh by being supported by the substrate 1, which serves as an outer frame, and suspended so as to be folded over itself in a heap. The conductive coating portion 3 is formed by forming the conductive coating 33 as a pattern over this fiber mesh. FIG. 3 illustrates the conductive coating 33 as dotted squares for convenience, but in actuality, it is formed by coating just one surface of the fiber mesh, at the relevant locations, with a metal or a compound having conductivity. The expression "one surface" refers to a surface on which the coating film is formed when a film is deposited from one surface.

The substrate 1 is not particularly limited as long as it functions as a support for the fiber mesh. The substrate 1 preferably has flexibility. In this case, "support" means that a portion of the fibrous resin composition 2 is fixed to one surface of the substrate 1. Additionally, as an example thereof, there are cases in which the fibrous resin composition 2 is held by the substrate 1 by straddling the aperture portion.

If the substrate 1 has pliability, then the flexibility of the electronic functional member 10 as a whole rises, thereby further increasing the surface conformability. For example, a generally used film or the like may be used as the substrate 1. For example, it is possible to use, as the substrate 1, polyethylene terephthalate (PET), polyimide (PI), polyvinyl chloride (PVC), polycarbonate (PC), polyethylene naphthlate (PEN), polyether ether ketone (PEEK) or the like. Additionally, it is possible to use, as the substrate 1, a stretchable material such as a fluoro rubber, a urethane rubber or a silicone rubber.

The thickness of the substrate 1 will differ depending on the type thereof, but should preferably be at least 1 μm and at most 1000 μm. If the thickness of the substrate 1 is at least 1 μm, it is possible to obtain sufficient strength as a support for suspending the fiber mesh. If the thickness of the substrate 1 is 1000 μm or less, it is possible to obtain high flexibility.

The aperture portion 1A may be formed in any area of the substrate 1, and the location thereof is not particularly limited. By having the aperture portion 1A, it is possible to pass gas and moisture through the aperture portion 1A, as well as to pass light.

The size of the aperture portion 1A is preferably at least 10 μm square and at most 10 cm square. If the size of the aperture portion 1A is too small, finer processing becomes necessary, and it becomes difficult to form the conductive coating portion 3 and the like on the fiber mesh. Additionally, the size of the aperture portion 1A is too small, the gas and moisture permeability through the aperture portion 1A become lower. On the other hand, if the aperture portion 1A is too large, it becomes difficult to support the fiber mesh with the substrate 1 as the outer frame.

The shape of the aperture portion 1A does not need to be square, and may be circular or the like. In the case of a circle, the diameter should preferably be at least 10 μm and at most 10 cm.

The resin composition 2 is suspended over the aperture portion 1A with the substrate 1 surrounding the aperture portion 1A as the outer frame. The fiber mesh is formed by heaping the resin composition 2, and there are voids in the resin composition 2. For this reason, the fiber mesh is highly gas and moisture permeable, so problems such as deviations in measurements or separation from the contact surface due to moisture from perspiration or the like can be prevented. In other words, highly precise measurements can be made over a long period of time. Additionally, it is possible to reduce discomfort and the like due to long-term attachment.

When observed closely, the conductive coating portion 3 is formed from a mesh-shaped conductive coating 33 formed on the resin composition 2 and voids in the fiber mesh in which this conductive coating 33 is formed. The conductive coating portion 3 is transparent due to these voids, so the surface being measured, with which the conductive coating portion 3 comes into contact, can be observed from above the conductive coating portion 3. Due to this structure, for example, when using the conductive coating portion 3 to detect the electrical properties at a specific location on the surface to be measured, it is possible to precisely determine the position of the conductive coating portion 3. Additionally, if the surface to be measured comprises living cells, it is possible to apply optical stimulation to the cells at a specific area through the conductive coating portion 3, and to measure the response to the optical stimulation at the conductive coating portion 3.

Additionally, it is possible to select the resin composition 2 itself that is to be used to form the fiber mesh, and thus to obtain a fiber mesh having excellent pliability and stretchability. At this time, the stretchability of the resin composition 2, where the conductive coating 33 has been formed, will be reduced by the presence of the conductive coating 33. However, since the periphery of the conductive coating portion 3 is suspended from the substrate 1 by means of the resin composition 2, the fiber mesh formed on the aperture portion 1A is pliable and stretchable, and furthermore, since the fiber mesh has voids, it is possible to obtain even better pliability and stretchability, and to raise the surface conformability and the stretchability.

The resin composition 2 in the fiber mesh is preferably partially interlinked. If the resin composition 2 is interlinked, the strength of the fiber mesh can be raised. Additionally, as explained below, the conductive coating portion 3 is formed on one surface of the fiber mesh. If the resin composition 2 is interlinked, the conductive coating 33 that is formed on one surface thereof will also be interlinked. Thus, the conductive coating 33 formed on the fiber mesh is made electrically continuous, and it is possible to prevent the occurrence of contact resistance or the like, or the connection of the conductive coating portion 3 being broken.

The material of the resin composition 2 is not particularly limited as long as it can be formed into fibers. For example, it is possible to use commonly used elastomers such as fluoro rubbers, urethane rubbers and silicone rubbers, or polymer materials other than elastomers such as acrylic, nylon and polyester. Among these, it is preferable to use an elastomer as the material of the resin composition 2. Elastomers are soft and have extremely little change in mechanical properties even when repeatedly subjected to intense strain. For this reason, high surface conformability and long-term attachment are possible.

When using the electronic functional member 10 on a living body, it is preferable for the resin composition 2 to comprise a substance that is tacky or adhesive to the living body. Since the fiber mesh comprising the resin composition 2 is fixed to the living body, it can then conform to deformations caused by movement of the living body, thereby providing highly precise measurements that are stable for a long period of time, without easily coming loose. Furthermore, it should preferably comprise a substance that can dissolve. After the electronic functional member 10 is brought into close contact with the living body, the conductive coating portion 3 is supported by the living body, so there is no need for it to be supported by the fiber mesh. For this reason, if the resin composition 2 is biodissolvable, then the resin composition 2 will dissolve after the electronic functional member 10 is brought into close contact with the surface of the living body, leaving the conductive coating portion 3 that is formed on the resin composition 2 in direct contact with the living body. If the living body and the conductive coating portion 3 are in direct contact, it is possible to better prevent the generation of resistance and to make measurements with higher precision. As examples of biodissolvable substances, it is possible to use polyvinyl alcohol (PVA), polyvinyl pyrrolidone (PVP), polyglycolic acid (PGA), polylactic acid (PLA) or the like. Additionally, the resin composition 2 does not need to completely biodissolvable. By partially dissolving, it is possible to improve the adhesion to the living body without lowering the strength of the fiber mesh. Aside therefrom, substances that have high adhesiveness and tackiness with respect to the living body can be favorably used.

The overall thickness of the fiber mesh is preferably at least 1 μm and at most 100 μm. In this case, the overall thickness of the fiber mesh refers to the thickness from one surface to the other surface of the fiber mesh. The overall thickness of the fiber mesh can be measured, for example, as the size of the gap when the fiber mesh is clamped between flat plates. If the fiber density is extremely low, the thickness becomes difficult to measure and define. However, if the fiber density is extremely low, it is not possible to secure adequate conductivity, so such a situation does not need to be considered.

If the overall thickness of the fiber mesh is at least 1 μm, the fiber mesh has sufficient strength. On the other hand, if the overall thickness of the fiber mesh is at most 100 μm, the resistance between the conductive coating portion 3 and the surface being measured can be safely ignored. Additionally, when used on a living body, the time needed for the living body to dissolve the resin composition 2 can be shortened.

The aperture ratio of the aperture portion 1A is preferably 10% to 99%. The fiber mesh has portions where the resin composition 2 is formed and portions consisting of voids. For this reason, the "aperture ratio of the aperture portion 1A" refers to the ratio of the portions where the voids are formed in plan view. The coating ratio is determined by photographing the surface of the fiber mesh at 10 arbitrary points having a size of 1 mm×1 mm, then determining the area of portions in the photographs in which the resin composition 2 is formed, and determining the average value thereof. If the aperture ratio of the aperture portion 1A is too low, then the gas and moisture permeability are decreased. On the other hand, if the aperture ratio of the aperture portion 1A is too high, the conductive coating portion 3 to be mentioned below becomes sparse and it becomes difficult to secure sufficient conductivity.

The resin composition 2 forming the fiber mesh preferably has a diameter of 100 nm to 10 μm, and more preferably 200 nm to 2000 nm. If the diameter is within this range, the strength is sufficient and it is possible to obtain an electronic functional member 10 having high gas and moisture permeability. The diameter of the resin composition 2 can be determined by using a scanning electron microscope to measure the cross section of the resin composition at 10 arbitrary points, then determining the average value of the diameters thereof.

The conductive coating portion 3 is patterned so as to coat one surface of the fiber mesh in a portion located over the aperture portion 1A, and to extend onto the substrate. For this reason, there are no connection portions at the interface between the substrate 1 and the fiber mesh, so the occurrence of contact resistance or the like can be prevented. Additionally, it is possible to prevent damage to electrical connections (such as the connection portions being broken) due to deformation of the substrate or the like, which was a problem in conventional electronic functional members. In order to make the connection of the conductive coating 33 formed on the substrate 1 and the fiber mesh highly reliable and sure, the substrate 1 and the resin composition 2 must be firmly bonded, and the conductive coating 33 must be formed with sufficient continuity across the resin composition 2 and the substrate 1.

Figure 4:
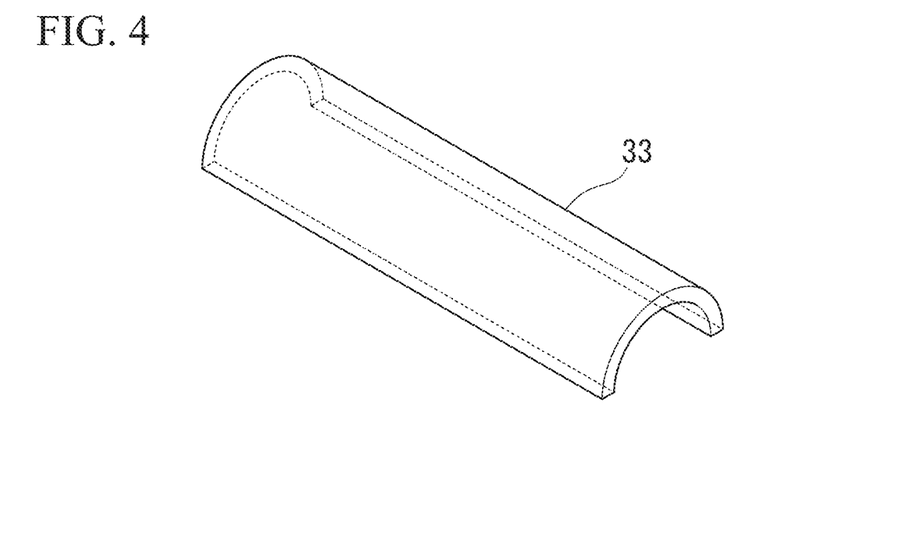
FIG. 4 is a schematic perspective view of a conductive coating portion formed on one fiber of a fiber mesh, with said fiber removed to show only the conductive coating portion.

FIG. 4 is a perspective view schematically showing only the conductive coating 33 with the fiber mesh removed from the conductive coating portion formed on one fiber in the fiber mesh. As shown in FIG. 4, the conductive coating 33 formed on one surface of the resin composition 2 has a semicircular arc-shaped structure. Since the resin composition 2 forming the fiber mesh has a circular cross-section, the conductive coating 33 is blocked by the resin composition 2 itself and is formed on only one surface of the resin composition 2. Since one surface of the resin composition 2 is semicircular arc-shaped, the conductive coating 33 also becomes semicircular arc-shaped.

FIGS. 2e and 2f in Non-Patent Document 1 indicate the strength of a conductive coating portion with respect to deformation. FIG. 2e in Non-Patent Document 1 is a drawing showing the rate of increase in the resistance value when a conductive coating portion is formed on a film and subjected to multiple bendings. FIG. 2f in Non-Patent Document 1 is a drawing showing the rate of increase in the resistance value when a conductive coating portion is formed on a film and pulled in the planar direction in which the conductive coating portion is formed. It can be understood that the conductive coating portion 3 has less resistance change due to deformation in comparison to ITO, and can function as an excellent transparent electrode.

The conductive coating portion 3 merely needs to be conductive. For example, a metal such as copper, gold, aluminum silver or zinc, or an organic conductive material, typically PEDOT/PSS, may be used. In view of the conductivity, copper and silver are particularly preferred. Additionally, when used on a living body or the like, it is preferable to use gold, which is stable, in order to prevent unwanted reactions.

The thickness of the conductive coating 33 of the conductive coating portion 3 is preferably 20 nm to 2000 nm, more preferably 20 to 1000 nm, and even more preferably 50 nm to 100 nm. If the thickness is within said ranges, sufficient conductivity and pliability are obtained. Since voids are formed in the conductive coating portion 3, the conductive coating area transmits light, so the state of the surface being contacted can be confirmed during measurement. The thickness of the conductive coating 33 can be measured by the same method as that used to measure the diameter of the resin composition 2 in the fiber mesh.

If the conductive coating 33 is thin, the conductive coating portion 3 can easily break when stress is applied to the fiber mesh. This is because the difference in rigidity between the resin composition 2 where the conductive coating 33 is formed and the resin composition 2 where it is not formed is small, so strain is applied to the conductive coating 33, making it more susceptible to breaks. On the other hand, if the conductive coating 33 is thick, the resin composition 2, which has lower rigidity relative to the surrounding conductive coating portion 3, becomes strained, so the stress acting on the conductive coating 33 can be relieved.

The elastic modulus of the metal forming the material of the conductive coating 33 is several tens of times greater than the elastic modulus of the resin composition 2. Therefore, the tensile rigidity is defined by the cross-sectional area of the conductive coating 33. If the electronic functional member can withstand 30% elongation, it can be practically used in many biometric applications. By holding the strain on the conductive coating 33 to 0.2%, it is possible to obtain high resistance to repeated deformation. In other words, the strain on the conductive coating 33 is held to just $\frac{1}{150}$ of the strain on the resin composition 2. It is preferable to use polyurethane as a resin composition 2 having high stretchabiliy. In this case, it is preferable for the elastic modulus of the conductive coating 33 to be approximately 100 to 300 times that of the resin composition 2, and the cross-sectional area of the conductive coating 33 to be at least 0.5 times the cross-sectional area of the resin composition 2. Specifically, the fiber diameter of the resin composition 2 should be set to be 500 nm and the conductive coating should be formed so as to have a thickness of 300 nm.

The shape of the conductive coating layer 3 is not particularly limited, and may be modified as needed. For example, when obtaining information from the brain of a living body, the conductive coating portion 3 may be patterned in accordance with the areas of the brain controlling the various functions in the living body. By bringing the patterned conductive coating portion 3 into contact with the areas of the brain of the living body controlling various functions, it is possible to obtain electrical signals from the contacted portions, and to thereby observe how the areas function.

(Electronic Functional Member Production Method)

The electronic functional member 10 is produced by performing a step of forming an aperture portion 1A in a substrate 1; a step of forming a fiber mesh by ejecting a resin composition, in the form of a fiber, onto the aperture portion 1A by means of electrospinning deposition; and a step of forming a conductive coating portion 3 extending across the substrate 1 and the fiber mesh. The electronic functional member production method will be explained with reference to FIG. 5.

The method for forming the aperture portion 1A in the substrate 1 is not particularly limited. For example, it may be cut by means of a cutter or the like. When doing so, it is preferable to provide a support on the rear surface of the substrate 1. By providing a support S, it becomes easier to form the aperture portion 1A. Additionally, the substrate 1 can be supported during a step of forming the fiber mesh to be described below. As the support S, it is possible to use glass, a resin film or the like.

Figure 5:
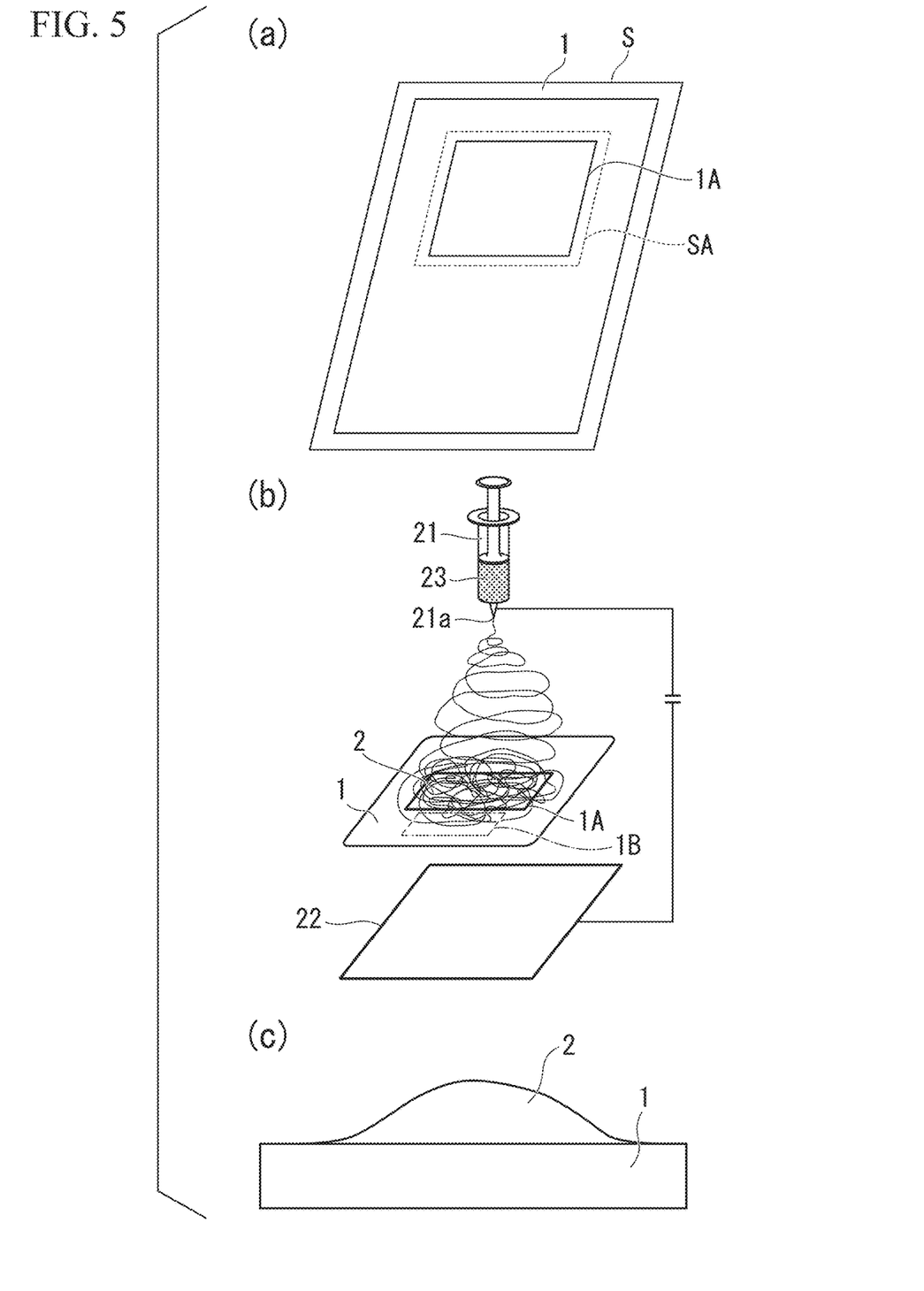
FIG. 5 is a schematic view of the process for producing the electronic functional member of the present invention.

When using a support S, as shown in FIG. 5(a), the aperture portion SA formed on the support S is formed towards the outside so as to enclose the aperture portion 1A provided in the substrate 1. This is so that, in the step of forming the fiber mesh, the fibers will be suspended over the substrate 1 from the window formed in the substrate. If the support is exposed on the inside of the aperture portion 1A, the fiber mesh will adhere to the support and problems such as the fiber mesh being broken during the process of peeling the substrate 1 from the support can occur. Additionally, the aperture portion 1A and the edges of the aperture portion opened in the support can be completely aligned. In that case, it is preferable for the edges of the support to overhang from the rear side of the support towards the front side on which the substrate 1 is laminated, so that the aperture portion 1A and the aperture portion of the support 1 are aligned at the lamination surface. The overhang can be formed by a method of simultaneously forming the aperture portion SA in the support S and the aperture portion 1A of the substrate 1 by means of laser cutting from the rear side of the support.

Next, the fiber mesh is formed by ejecting the resin composition onto the aperture portion 1A by electrospinning deposition. FIG. 5(b) is a schematic view of the electrospinning deposition method.

Electrospinning deposition involves extruding a solution 23 from a syringe 21 while applying a high voltage between a needle 21a on the syringe 21 and a conductive sheet 22. At this time, the potential difference between the needle 21a and the conductive sheet 22 causes the solution 23 to be suddenly drawn from the syringe 21 and sprayed towards the conductive sheet 22. By sandwiching the substrate 1 in which the aperture portion 1A is formed between the syringe 21 and the conductive sheet 22, the sprayed solution 23 forms the resin composition 2 so as to be suspended over the aperture portion 1A of the substrate 1, thereby generating the fiber mesh. The solution 23 contains the resin composition 2 dissolved in a solvent, and the solvent is mostly evaporated between the needle 21a and the aperture portion 1A.

In contrast therewith, it is preferable for the resin composition 2 to contain a small amount of the solvent immediately after being suspended over the aperture portion 1A. In other words, it is preferable for the solvent to not be completely evaporated at the suspension stage. If a small amount of the solvent remains at the time of suspension over the aperture portion 1A, the resin composition 2 forming the fiber mesh will be partially linked when the solvent evaporates. If the resin composition 2 is interlinked, then the strength of the fiber mesh can be raised. Additionally, as mentioned below, the conductive coating portion 3 is formed on one surface of the fiber mesh. If the resin composition 2 is interlinked, then the conductive coating portion 3 formed on a surface thereof will be interconnected. For this reason, the conductive coating portion 3 can be formed as a single body and the occurrence of contact resistance or breakage of the conductive coating during deformation can be prevented. The distance between the needle 21a and the aperture portion 1A is preferably 10 cm to 50 cm. Additionally, because the solvent remains, the resin composition 2 formed on the substrate 1 becomes semicircular. FIG. 5(c) shows a schematic section view of the resin composition 2 formed in the area 1B surrounded by the single-dotted chain line in FIG. 5(b). By having such a shape, when the conductive coating portion 3 is formed so as to extend from the resin composition 2 to the substrate 1, it is continuously formed without the conductive coating 33 being broken.

The conductive coating portion 3 is formed by patterning on one surface of the fiber mesh 2 in a portion located over the aperture portion 1A, and so as to extend onto the substrate. The method for forming the conductive coating portion 3 is not particularly limited. For example, vapor deposition, sputtering, chemical vapor deposition or the like may be used. The shape of the conductive coating portion 3 can be arbitrarily modified by patterning. As the patterning method, film deposition through a mask is the simplest method and is preferred.

Figure 6:
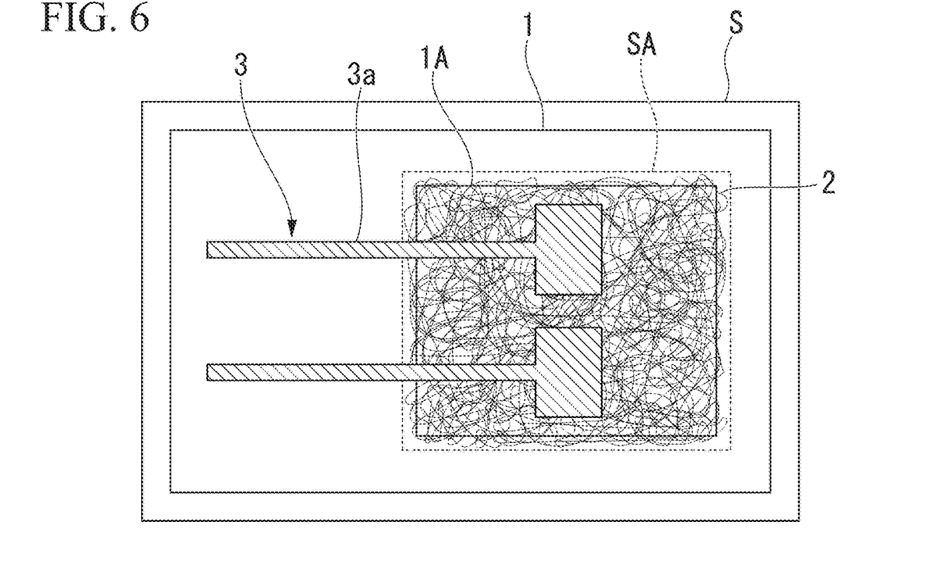
FIG. 6 is a schematic view of an electronic functional member according to another embodiment of the present invention.

Additionally, when the pattern of the conductive coating portion 3 includes thin wiring portions 3a as shown in FIG. 6, it is preferable for the size of the holes in the fiber mesh to be ⅕ or less of the minimum size of the pattern of the conductive coating portion 3 so as not to lose the continuity in the conductive coating.

The method for producing the electronic functional member 10 is not limited to the above method. For example, instead of forming the fiber mesh directly on the aperture portion 1A by electrospinning, the fiber mesh may be formed on a different component and then transferred later. Specifically, the fiber mesh is formed by electrospinning on a large ring-shaped conductive member so as to be suspended from the ring. If a substrate 1 having an aperture 1A is then passed through this ring from one side to the other, the fiber mesh becomes entangled on the substrate 1. As a result thereof, a ring-shaped fiber mesh is transferred to the aperture portion 1A, thereby forming the fiber mesh on the aperture portion 1A. Additionally, the method is not limited to electrospinning, and a method of producing a sheet comprising thin fibers, cutting the sheet, then laminating the sheet onto the substrate 1 so as to cover the aperture portion 1A may be used. In this case, the sheet comprising thin fibers becomes a non-woven fabric having voids. Additionally, by using a thermoplastic polymer as the fiber material, it can be easily laminated by thermocompression bonding.

Figure 10:
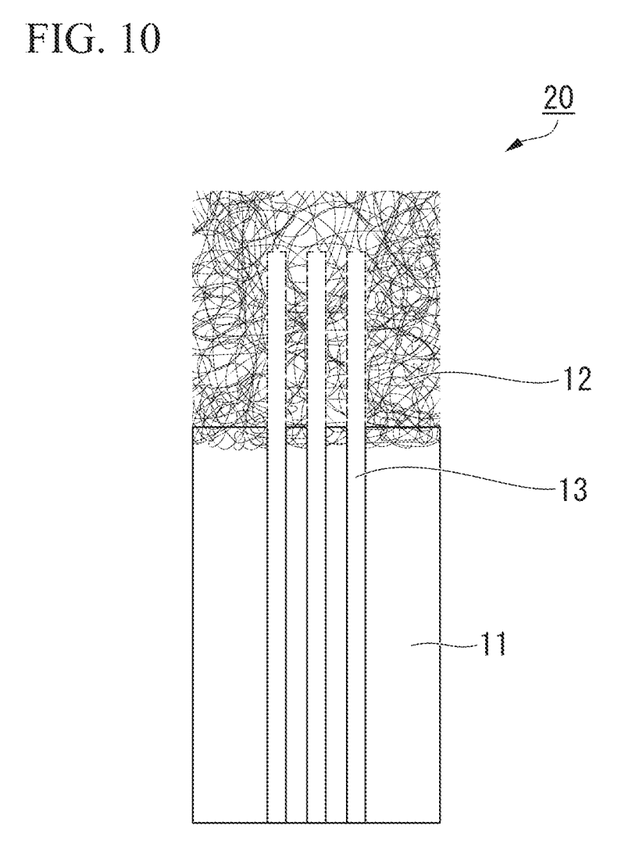
FIG. 10 is a schematic view of an electronic functional member according to another embodiment of the present invention.

Additionally, while an electronic functional member in which the substrate 1 has an aperture portion 1A has been explained up to this point, a structure not having an aperture portion 1A, as shown in FIG. 10, may be used.

The electronic functional member 20 shown in FIG. 10 comprises a substrate 11; a fiber mesh 12 comprising a fibrous resin composition that extends onto and is connected to the substrate 11; and a patterned conductive coating portion 13 that coats one surface of a portion of the fiber mesh and that also extends onto the substrate 11.

The fiber mesh 12 is merely connected to the substrate 11 and may not have sufficient strength. In that case, it is possible to provide a support S, as explained in connection with the above-mentioned production method, on the rear surface thereof. Until the electronic functional member 20 is affixed to the living body for actual use, it is supported on the support S and the strength can thus be maintained, and the support S is peeled at the time of actual use, thereby raising the conformability to the living body.

Additionally, the electronic functional member 20 shown in FIG. 10 is obtained by obtaining the electronic functional member 10 in FIG. 1 using a process similar to that in the above-mentioned production method, then removing the outer frame portion. The outer frame portion is cut away with a cutter or the like.

(Electronic Component)

The electronic component according to one embodiment has an electronic circuit element connected to the conductive coating portion of the above-mentioned electronic functional member. The electronic circuit element may be a transistor comprising an organic semiconductor layer or the like formed on the conductive coating portion, or may be an electronic circuit board on which separate electronic components are mounted.

For example, the electronic functional member has the conductive coating portion formed on a portion of the fiber mesh as mentioned above, and can be made to function as an organic transistor by laminating an organic semiconductor layer thereon.

When forming an organic semiconductor layer on the conductive coating portion 3, it is possible to use a mask similar to the mask used when laminating the conductive coating portion. Additionally, layers other than the organic semiconductor may also be laminated.

For example, a diode element can be formed by laminating a p-type semiconductor, an n-type semiconductor and opposing electrodes onto the conductive coating portion. The pn junction between the p-type semiconductor and the n-type semiconductor allows electricity to pass in one direction, but does not allow electricity to pass in the other direction. In other words, it can function as a switching element.

Additionally, it can be made to function as a photoelectric conversion element by using a similar structure. By irradiation with light from an external source, carriers can be generated in the interface between the p-type semiconductor and the n-type semiconductor, thereby generating an electric circuit. Conversely, it is possible to generate light by applying a voltage (solar cell element or the like).

Additionally, solar cells and the like are usually formed on substrates. Total reflection occurs on the outer surfaces of such substrates, so some of the light generated in the photoelectric conversion layer cannot be guided inside the substrate and extracted. However, since the area in which the organic semiconductor layer is formed in the present electronic component is the aperture portion, there is no need to consider the total reflection due to the substrate, and the light extraction efficiency can be raised.

Figure 7:
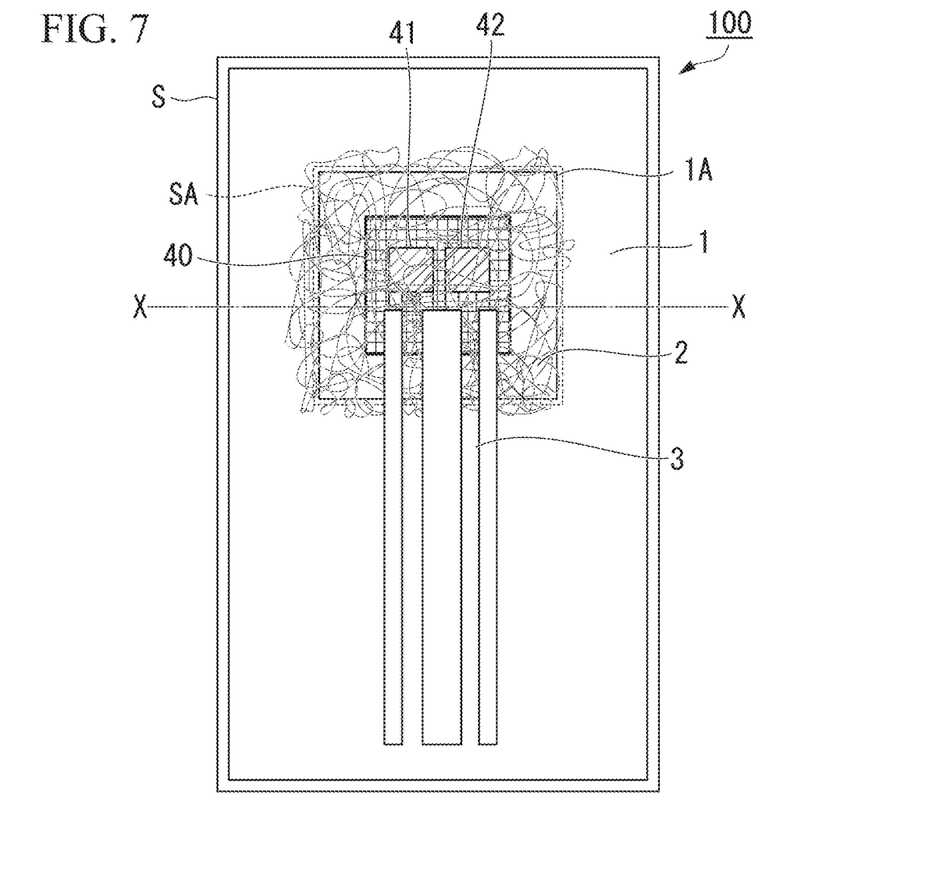
FIG. 7 is a schematic view of an electronic component according to an embodiment of the present invention.

FIG. 7 is a schematic view of an electronic component according to one embodiment of the present invention. In the electronic component 100 according to the one embodiment, an electronic substrate (electronic circuit element) 40 having electronic components formed or mounted on a substrate 1 is installed in the aperture portion 1A in the substrate 1. The electronic substrate 40 is suspended by a fiber mesh comprising a resin composition 2. Additionally, a light-emitting element 41 and a light-receiving element 42 are provided on the electronic substrate 40, and electric terminals for electrically connecting to each are formed on the surface of the electronic substrate 40. The fiber mesh is formed so as to extend from the electronic substrate 40, on which the light-emitting element 41 and the light-receiving element 42 are provided, to the substrate 1, and the conductive coating portion 3 is formed as wiring on the fiber mesh. Although FIG. 7 also shows a support S, at the time of actual use, the support S is removed before use.

During the process of forming the fiber mesh over the electronic substrate 40, it is necessary for the electronic substrate 40 to be supported inside the aperture 1A. This is achieved by providing a substrate support portion extending from the aperture edges on the substrate 1 (omitted in the drawings), and laminating the electronic substrate 40 on the substrate support portion. After the fiber mesh has been formed, a portion of the substrate support portion may be cut with a laser or the like as needed, resulting in a state in which the electronic substrate 40 is freely suspended from the substrate 1.

(Wearable Device)

Figure 8:
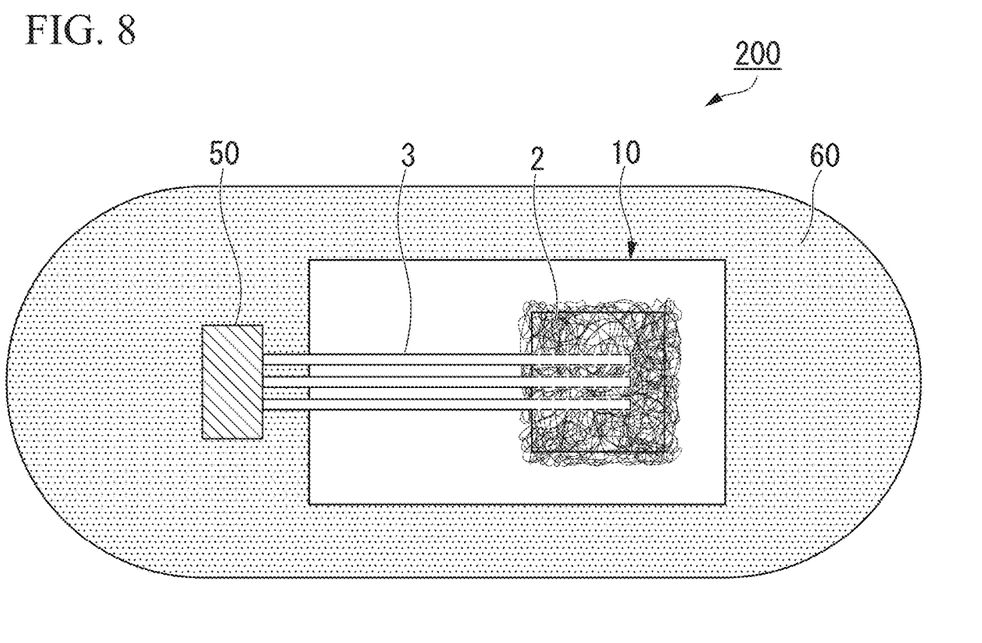
FIG. 8 is a schematic view of a wearable device according to an embodiment of the present invention.

The wearable device according to one embodiment comprises the above-mentioned electronic functional member 10. FIG. 8 is a schematic view showing the wearable device according to the one embodiment. The wearable device 200 shown in FIG. 8 comprises an electronic functional member 10; an integrated circuit 50 that is bonded by the conductive coating film 3 on the electronic functional member 10; and a coating film 60 formed so as to coat the electronic functional member 10 and the integrated circuit 50.

The wearable device 200 comprises the above-mentioned electronic functional member 10, and therefore has excellent surface conformability and stretchability. For this reason, it is possible to obtain a wearable device lacking a sense of attachment. Additionally, the gas and moisture permeability are high, so it is possible to prevent problems such as deviations in measurements or separation from the contact surface due to moisture from perspiration or the like, and to take stable measurements over a long period of time.

The integrated circuit 50 receives information from the surface being measured, as measured by the electronic functional member 10, via the conductive coating portion 3. The integrated circuit 50 can transmit the obtained information to a receiver (omitted from the drawing) by means of wireless transmission or the like. As a result thereof, it functions as a wearable device.

The electronic functional member 10 and the integrated circuit 50 are coated by the coating film 60. By providing the coating film 60, it is possible to block out external influences. Additionally, it is possible to improve the adhesion of the wearable device 200 to the attachment surface, and to make stable measurements over a long period of time. The coating film 60 can preferably selectively pass gas and moisture, though this will also depend on the mode of use. For example, when used on land or the like, it is preferable for the gas and moisture that has passed through the electronic functional member 10 to be able to be directly discharged to the outside. In contrast, when used in water or the like, it should preferably be able to block some moisture in order to prevent external moisture penetrating into the electronic functional member 10.

The integrated circuit 50 is not particularly limited. Any common type may be used as long as it is able to transmit information to the outside. The coating portion 60 may also be of a type that is generally used in adhesive bandages or the like.

EXAMPLES

Example 1

Figure 9:
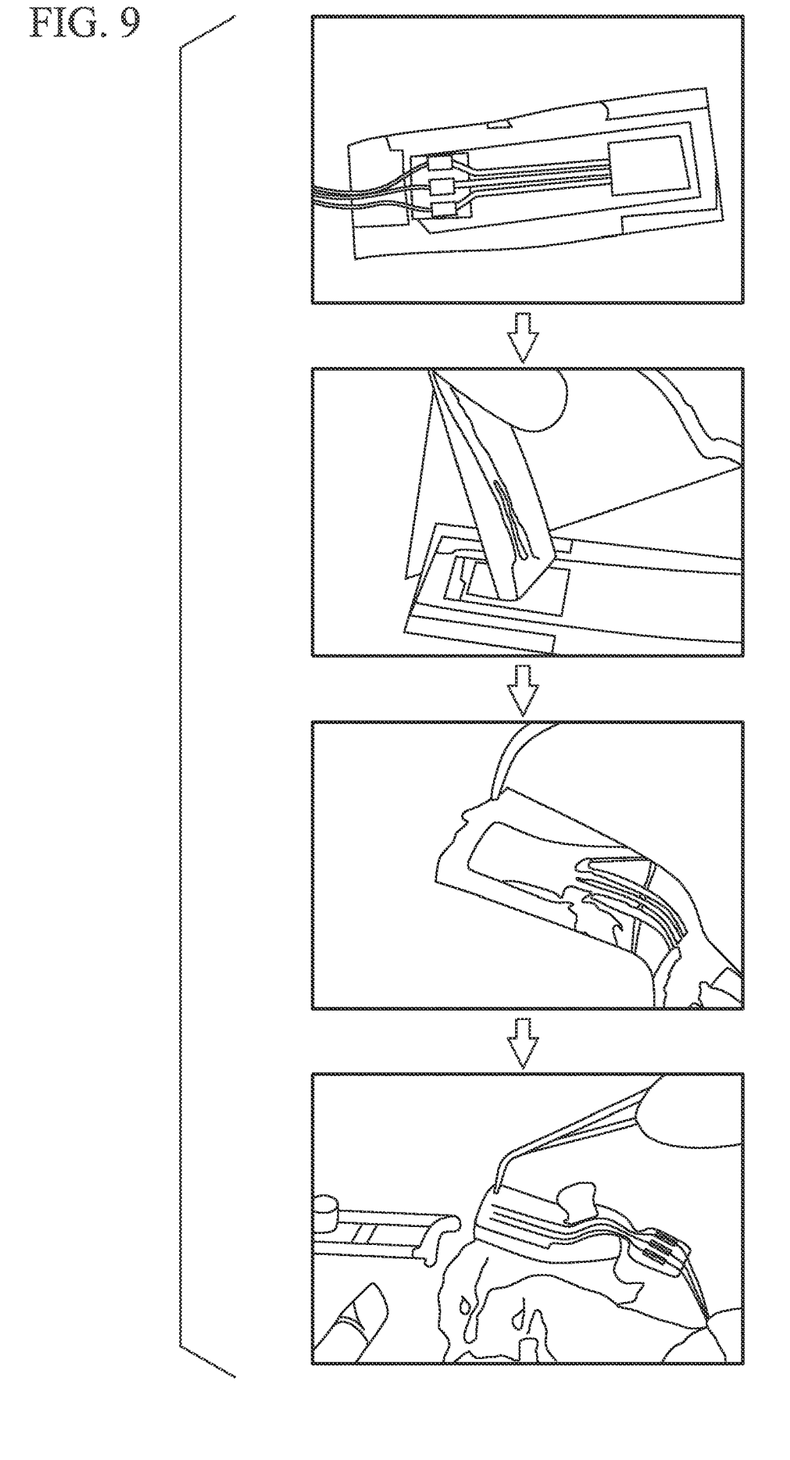
FIG. 9 shows steps for producing and using an electronic functional member in an example.

FIG. 9 shows the procedures for producing and using an electronic functional member according to an example.

The substrate was formed from a film comprising parylene, and a 1 cm×2 cm aperture portion was formed therein. At this time, a polyimide film having an aperture portion of the same size formed therein was used as a support on the rear surface of the parylene.

Next, a resin composition was suspended over the aperture portion by using an electrospinning method. The resin composition was formed from PVA, and the resin composition had a diameter of 300 to 800 nm, with some slight variation thereof.

Furthermore, a conductive coating portion was formed as a single body extending from the fiber mesh comprising the resin composition to the substrate. The conductive coating portion was formed by vapor deposition through an Au mask. Due to the mask, the conductive coating portion was formed as three terminals on the fiber mesh. The film thickness of the conductive coating portion was 80 nm.

Next, the electronic functional member was peeled from the support. This electronic functional member was brought into contact with the brain of a rat. At this time, the resistance measured across the electrodes was 4 to 12 kΩ.

Comparative Example 1

In the electronic functional member of Comparative Example 1, an Au film was formed, as three terminals through a mask, on a film comprising parylene. Comparative Example 1 differed from Example 1 in that it did not have an aperture portion and did not have a fiber mesh. The electronic functional member of this Comparative Example 2 was used to perform tests similar to those in Example 1, whereupon the resistance value measured across the electrodes was 100 kΩ to 1 MΩ.

Comparing Example 1 with Comparative Example 1, it can be understood that the resistance value of Example 1 was measured as being smaller. This is considered to be because, in Comparative Example 1, the film was composed of Au and therefore could not sufficiently conform to the surface being measured on the living body. In contrast therewith, Example 1 had higher conformability due to the fiber mesh and was therefore able to make more precise measurements.

Example 2

An electronic functional member was produced in the same manner as in Example 1. The produced electronic functional member was attached to the surface of skin on the human body, and the resistance value was measured. As a result thereof, measurements were able to be made even after two weeks had elapsed after attachment to the skin. In other words, the adhesive force did not decrease even when coming into contact with perspiration from the human body or the like, or moisture to which the human body is exposed in everyday life. This is considered to be because the electronic functional member was soft and resistant to deformation, and also was permeable to gas, moisture and light.

REFERENCE SIGNS LIST

1 Substrate
1A Aperture portion
2 Resin composition
3 Conductive coating portion
3a Wiring portion
10 Electronic functional member
21 Syringe
21a Needle
22 Conductive sheet
23 Resin composition
33 Conductive coating
40 Electronic substrate
50 Integrated circuit
60 Coating film
100 Electronic component
200 Wearable device

The invention claimed is:

1. An electronic functional member comprising:
a substrate;
a fiber mesh comprising a fibrous resin composition that extends onto and is connected to the substrate; and
a patterned conductive coating portion that coats one surface of a portion of the fiber mesh and that also extends onto the substrate, wherein the patterned conductive coating portion is formed from a mesh-shaped conductive coating formed on the fibrous resin composition, and a plurality of voids in the fiber mesh in which the mesh-shaped conductive coating is formed.

2. An electronic functional member comprising:
a substrate having an aperture portion;
a fiber mesh comprising a fibrous resin composition that is suspended over the aperture portion with the substrate around the aperture portion as an outer frame; and
a patterned conductive coating portion that coats one surface of a portion of the fiber mesh located over the aperture portion, and that also extends onto the substrate.

3. The electronic functional member according to claim 1, wherein the resin composition is partially interlinked.

4. The electronic functional member according to claim 1, wherein the resin composition comprises a substance that is biodissolvable.

5. The electronic functional member according to claim 2, wherein the aperture portion has an aperture ratio of 10% to 99%.

6. The electronic functional member according to claim 1, wherein the conductive coating forming the conductive coating portion has a film thickness of 20 nm to 2000 nm.

7. An electronic component having an electronic element connected to the conductive coating portion of the electronic functional member according to claim 1.

8. A wearable device comprising the electronic functional member according to claim 1.

* * * * *